(12) United States Patent
Chaussin et al.

(10) Patent No.: US 9,329,163 B2
(45) Date of Patent: May 3, 2016

(54) DEVICE FOR SENSING A PARAMETER RELATED TO AN ELECTRICAL PHENOMENON OF BIOPHARMACEUTICAL CONTENT AND BIOPHARMACEUTICAL CONTAINER COMPRISING SUCH A SENSING DEVICE

(75) Inventors: Sebastien Chaussin, Aubagne (FR); Martin Heule, Vleuten (NL)

(73) Assignee: SARTORIUS STEDIM FMT SAS, Aubagne (FR)

(*) Notice: Subject to any disclaimer, the term of this patent is extended or adjusted under 35 U.S.C. 154(b) by 413 days.

(21) Appl. No.: 13/807,943

(22) PCT Filed: Jul. 1, 2011

(86) PCT No.: PCT/FR2011/051541
§ 371 (c)(1),
(2), (4) Date: Feb. 7, 2013

(87) PCT Pub. No.: WO2012/001322
PCT Pub. Date: Jan. 5, 2012

(65) Prior Publication Data
US 2013/0139618 A1    Jun. 6, 2013

(30) Foreign Application Priority Data
Jul. 2, 2010    (FR) ..................................... 10 55403

(51) Int. Cl.
*G01N 33/48* (2006.01)
*C12M 1/00* (2006.01)
(Continued)

(52) U.S. Cl.
CPC .............. *G01N 33/48* (2013.01); *C12M 23/26* (2013.01); *C12M 23/28* (2013.01); *C12M 41/36* (2013.01)

(58) Field of Classification Search
CPC ........... G01N 27/221; G01N 2001/002; G01R 25/00; H05K 13/027
USPC ............ 73/864, 863.52, 863.57; 36/102, 140, 36/142
See application file for complete search history.

(56) References Cited

U.S. PATENT DOCUMENTS

| | | |
|---|---|---|
| 3,710,237 A | 1/1973 | Watson et al. |
| 7,241,369 B2 | 7/2007 | van Hoorn |

(Continued)

FOREIGN PATENT DOCUMENTS

| | | |
|---|---|---|
| DE | 4040333 A1 | 9/1991 |
| DE | 102006022290 A1 | 11/2007 |

(Continued)

OTHER PUBLICATIONS

International Search Report dated Nov. 29, 2011, corresponding to PCT/FR2011/051541.

*Primary Examiner* — John Fitzgerald
*Assistant Examiner* — Anthony W Megna Fuentes
(74) *Attorney, Agent, or Firm* — Young & Thompson (57) ABSTRACT

The sensing device (12) includes support and fixing elements (13), elements (14) for capturing the parameter, fixed rigidly to the support and fixing elements (13), including a sensing face (14*a*), situated in a chamber (17), a solid internal chamber end wall (30) disposed transversely, an open part (18) made in the chamber peripheral wall (27), the chamber (17) being a holding chamber (17) able to ensure confinement of the content (C) therein, and being isolated from the inside space (3*a*) of the container and safeguarded from the agitation prevailing therein, by the internal end wall (30) of the chamber so as to minimize the impact of this agitation on the measurement of the parameter of the content (C) by the sensing face (14*a*).

31 Claims, 7 Drawing Sheets

(51) Int. Cl.
    *C12M 1/02*     (2006.01)
    *C12M 1/34*     (2006.01)

(56) References Cited

U.S. PATENT DOCUMENTS

| | | |
|---|---|---|
| 7,489,402 B2 | 2/2009 | Selker et al. |
| 2007/0157748 A1 | 7/2007 | Baumfalk |
| 2008/0171383 A1 | 7/2008 | Selker et al. |
| 2009/0207689 A1* | 8/2009 | Artusi .......................... 366/140 |
| 2011/0101997 A1* | 5/2011 | Gulbranson ................. 324/664 |
| 2011/0187388 A1 | 8/2011 | Ossart |

FOREIGN PATENT DOCUMENTS

| | | | |
|---|---|---|---|
| EP | 0 810 281 | 12/1997 | |
| EP | 1396718 B1 | 3/2004 | |
| FR | 2934371 A1 | 1/2010 | |
| GB | 2283572 A | 5/1995 | |
| WO | 0026661 A1 | 5/2000 | |
| WO | 02090962 A1 | 11/2002 | |
| WO | 2005/068059 | 7/2005 | |
| WO | 2006107728 A1 | 10/2006 | |
| WO | 2008/153401 | 12/2008 | |
| WO | 2009/071829 | 6/2009 | |
| WO | WO 2009116002 A1 * | 9/2009 | ............... B01F 3/04 |
| WO | 2010/010313 | 1/2010 | |

* cited by examiner

DEVICE FOR SENSING A PARAMETER RELATED TO AN ELECTRICAL PHENOMENON OF BIOPHARMACEUTICAL CONTENT AND BIOPHARMACEUTICAL CONTAINER COMPRISING SUCH A SENSING DEVICE

BACKGROUND OF THE INVENTION

1. Field of the Invention

The invention relates to the sensing of a parameter related to an electrical phenomenon in a biopharmaceutical content located in the internal space of a biopharmaceutical container, able to be translated into an electrical signal.

2. Description of the Related Art

Its subject matter is more especially firstly a device for sensing a parameter related to an electrical phenomena and able to be translated into an electrical signal of a biopharmaceutical content located in the internal space of biopharmaceutical container and secondly a biopharmaceutical container comprising such a sensing device.

"Parameter related to an electrical phenomenon" means a parameter that is either per se of an electrical nature such as conductivity, impedance or capacitance, or is obtained by a process dependent on a variable of an electrical nature such as temperature (by means of a thermocouple or resistance probe).

The document WO 2008/153401 describes a flexible bioreactor the flexible wall of which at the bottom part is interrupted by a rigid element connected sealingly to the flexible wall, the rigid element comprising means of measuring the cell activity in the bioreactor in operation non-invasively. These measurement means aim to measure the oxygen, pH or conductivity. The bioreactor is intended to be carried and fixed to a tilting platform. In a first embodiment, these measurement means are arranged in an overhang directly penetrating the content of the bioreactor and directly facing it. In a second embodiment, a measurement receptacle is provided in which the measurement means are placed. In this embodiment, the measurement means are surrounded by a laterally closed wall constituting the receptacle, which is completely open in its internal end part. Thus this measuring receptacle always contains a certain quantity of liquid, even when the bioreactor tilts with the tilting platform. In neither cases, the presence of a mixing member such as a screw inside the bioreactor is provided for and consequently there is no impact on the measurement arising from the presence of such a mixing member, being here non-existent, that would have to be overcome.

Document EP 0 810 281 describes an apparatus for detecting and monitoring the development of a culture in a bioreactor that comprises, at the top part of the bioreactor, a chamber in which a plurality of sensors are placed, this chamber being open at the front. A mixing member such as a screw is also not provided for inside the bioreactor.

Document WO 2010/010313 describes a similar bioreactor wherein the impedance sensing part of the capacitive type is in direct contact with the inside of the bioreactor.

Document WO 2005/068059 describes a flexible mixing pouch intended to receive biopharmaceutical fluids in which located means of mixing and means of aerating the content of the pouch and means of sensing a parameter such as pH, oxygen level, temperature, etc are located, being also placed in an overhang directly penetrating the content of the pouch.

Document U.S. 2007/0157748 describes an arrangement for fixing a sensor on a support part fixed to the flexible wall of a mixing pouch.

Document WO 2009/071829 describes a device for connecting an accessory having an active part to a receptacle.

It has been found that, when a device for sensing a parameter related to an electrical phenomenon is associated with a biopharmaceutical container in which the biopharmaceutical content is subject to agitation—and more especially to a fairly powerful agitation—arising from the use of a mixing member located inside the container, the operation of the sensing device is disturbed by this agitation, so that the value of the parameter measured by the sensing device cannot always be the exact actual value of the parameter.

SUMMARY OF THE INVENTION

The purpose of the invention is therefore to provide a solution to this problem.

To this aim, and according to a first aspect of the invention, the subject matter of the invention is a device for sensing a parameter related to an electrical phenomenon and able to be translated into an electrical signal, such as in a biopharmaceutical content located in the space of a biopharmaceutical container delimited by a wall having an opening, the content being able to be subject to agitation, the sensing device having an axis, a proximal side towards the container and a distal side opposite to the container.

This sensing device comprises:

support and fixing means of a wall type, rigid, able to support the members constituting the sensing device and to be fixed rigidly and sealingly to the wall at the periphery of the opening, comprising a support and fixing wall and a set of chamber walls, delimiting a chamber for the content, having a closed part that includes an open part able to provide passage of the content between the chamber and the internal space of the container external to the chamber, said set of walls comprising an external chamber end wall, closed, disposed transversely, able to come in line with the opening, and at least one peripheral chamber wall, extending from its distal end part in an axial direction towards the proximal side from the periphery of the external end wall, and means of capturing the parameter, rigidly fixed to the support and fixing means, comprising a capture face located in the chamber, able to be in electrical contact with the content, and electrical connection means electrically connected to the sensing means, rigidly fixed to the support and fixing means, able to be accessible from the outside of the container when the sensing device is fixed to it and to be electrically connected to electrical connection means located outside the container.

This sensing device is such that said set of walls comprises an internal chamber end wall forming a rigid whole, solid, that is to say closed, disposed at least in part generally transversely in line with the external end wall from the proximal axial end part of the peripheral wall, the open part being provided in the peripheral wall. Thus the chamber is a holding chamber able to provide confinement of the content located therein, the chamber being isolated from the internal space and preserved from the agitation prevailing therein by the internal chamber end wall, solid, that is to say closed, so as to minimise the impact of this agitation on the measurement of the parameter of the content by the capture face.

Thus an internal chamber end wall is provided and is solid, that is to say closed, whereas the open part is provided in the peripheral wall rather than in the internal chamber end wall.

According to one embodiment, the support and fixing wall is at least partly roughly flat in shape, delimited by a peripheral external edge, one of the faces of which comprises a peripheral area for rigid sealed fixing to the wall of the container at the periphery of its opening.

According to one embodiment, the support and fixing wall and the external end wall are two functionally distinct parts of the same wall.

According to one embodiment, the external end wall and the support and fixing wall are offset in a roughly axial direction and connected to each other by a peripheral connecting wall, extending at least partly roughly in the axial direction, extending with respect to the support and fixing wall towards the distal side or towards the proximal side.

According to one embodiment, the sensing face is entirely located in the holding chamber on at least one face of the external end wall and/or one wall in the set of walls, and is turned towards the inside of the holding chamber. Thus the sensing face can be located on the peripheral wall and/or on the internal end wall.

According to one embodiment, the sensing face is located in line with a closed part of the set of walls and/or the external end wall.

According to one embodiment, the sensing face is substantially flat and coplanar with the substantially flat internal face of the wall on which it is located.

According to one embodiment, the sensing face is close to a closed part of a wall facing the set of walls or the external end wall of the chamber and/or is distant from an open part.

According to one embodiment, the device comprises a plurality of means of capturing one or more parameters. For example, these capture faces are located on the face turned towards the inside of the holding chamber of the same wall or different walls.

According to one embodiment, the electrical connection means are carried by the support and fixing wall and/or the external end wall and/or the peripheral connecting wall.

According to one embodiment, the electrical connection means are housed in a protective cavity. For example, the protective cavity is delimited by the external end wall and either the peripheral connecting wall or a dedicated cavity wall.

According to one embodiment, the sensing device comprises a plurality of electrical connection means.

According to one embodiment, the sensing means are means of sensing the conductivity, impedance, capacitance and temperature of the biopharmaceutical content.

According to one embodiment, the support and fixing wall has a certain rigid strength.

According to one embodiment, the support and fixing means include at least one support or guide means able to support or guide at least one trunnion of a mixing means. For example, the at least one support and guide means is located on or carried by the support and fixing wall and/or the set of chamber walls. For example, the at least one support or guide means forms, with the support and fixing wall and/or the set of chamber walls, a blind bearing for the end of the at least one trunnion of a mixing means.

According to one embodiment, the sensing device is for single use.

According to a second aspect, the subject matter of the invention is a biopharmaceutical container of the type comprising one or more inlets and outlets, at least one mixing means, when applicable at least one aeration means, an internal space delimited by a wall having at least one passage and mounting opening for at least one sensing device, the biopharmaceutical content of the container being able to be subject to agitation, the at least one sensing device being fixed rigidly and sealingly to the container around the at least one passage opening and able to be in electrical communication firstly with the content and secondly with electrical connection means located outside the container, in which the at least one sensing device is a sensing device as previously described.

The at least one mixing means and where applicable the at least one aeration means, comprise at least one member located in the internal space.

According to one embodiment, a sensing device is close to the at least one mixing means and where applicable to the at least one aeration means.

According to one embodiment, the sensing device is located at the bottom part of the biopharmaceutical container.

According to one embodiment, the wall of the biopharmaceutical container has a certain flexibility.

According to one embodiment, the container is for single use.

According to the embodiments, the biopharmaceutical container constitutes a pouch for storing and/or filling and/or manipulating and/or transporting and/or mixing a biopharmaceutical content or a bioreactor for a biopharmaceutical content.

Several embodiments of the invention are now described with the help of the drawings, in which:

BRIEF DESCRIPTION OF THE DRAWING FIGURES

FIGS. 3 to 11 are nine partial schematic views in axial section of the bottom part of a biopharmaceutical container more especially illustrating the installation of a device for sensing a parameter related to an electrical phenomenon and able to be translated into an electrical signal with which a biopharmaceutical container is provided, this sensing device comprising a holding chamber, a capture face located in the holding chamber, support and fixing means comprising a support and fixing wall and a set of chamber walls itself including an external axial end wall, a peripheral wall and, as indicated, an internal chamber end wall that is solid, that is to say closed, the whole delimiting the holding chamber and having one or more closed parts including one or more open parts located in the peripheral wall, the figures corresponding to these schematic views illustrating various possible embodiments, indicative and non-limitative, able where applicable, unless incompatible, to be combined at least partly with one another, namely the embodiments in which the support and fixing wall and the external chamber end wall are two functionally distinct parts of the same wall (FIGS. 3 to 11), the external end wall of the chamber and the support and fixing wall are coplanar (FIGS. 3 to 5 and 7) or offset in the axial direction (FIGS. 6 and 8 to 11), the offset external chamber end wall is distal (FIGS. 8 to 11) or proximal (FIG. 6), the capture face is located on an external chamber end wall (FIGS. 3, 6 to 9 and 11) or on a peripheral chamber wall (FIG. 5) or on an internal chamber end wall (FIGS. 4 and 10) or on several walls (FIG. 11), the sensing device comprises a capture means (FIGS. 3 to 6, 8 to 10) or several capture means or several electrical connection means (FIGS. 7 and 11), the electrical connection means are housed in a protective cavity (FIG. 6), the support and fixing means of the sensing device include a means of supporting or guiding a trunnion of a mixing means (FIGS. 3 to 7, 10 and 11), which forms a blind end bearing (FIGS. 3 to 6, 10 and 11) or a through bearing (FIG. 7), the sensing device comprises an annular wall forming protection for the trunnion of the mixing means (FIG. 7).

DETAILED DESCRIPTION OF THE INVENTION

Figure 1:
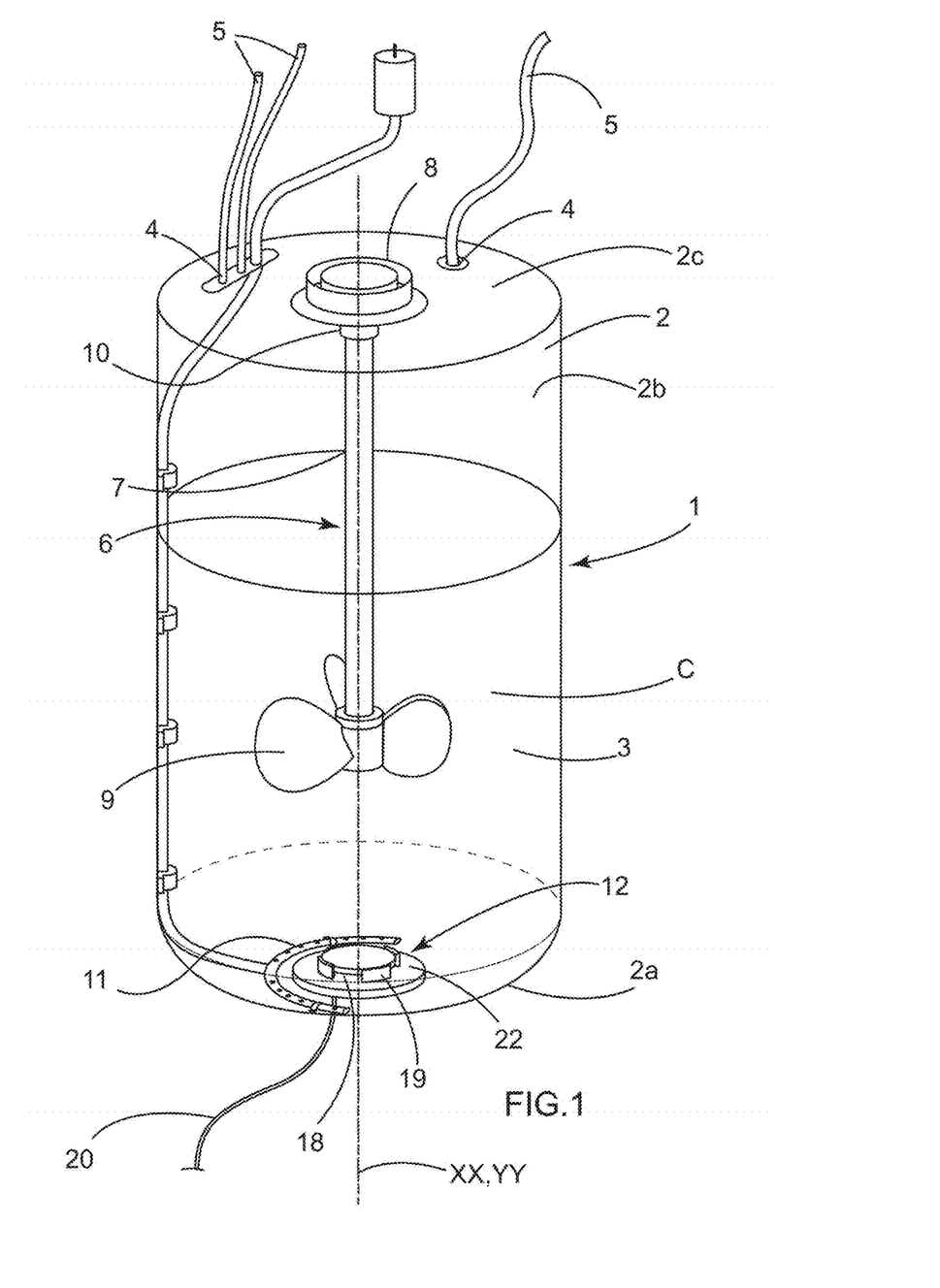
FIG. 1 is a schematic view in perspective of a possible embodiment of a biopharmaceutical container such as a bioreactor, the rigid external holding device of which is not shown.

FIG. 1 shows a biopharmaceutical container 1 being here a bioreactor intended to receive a biopharmaceutical content C comprising a liquid phase and cells, microorganisms, etc, with a view to a bioreaction that may be monitored and controlled by measuring the biomass in the bioreactor 1. For this purpose, an aim is to measure a parameter representing the biomass, such as for example impedance.

Figure 2:
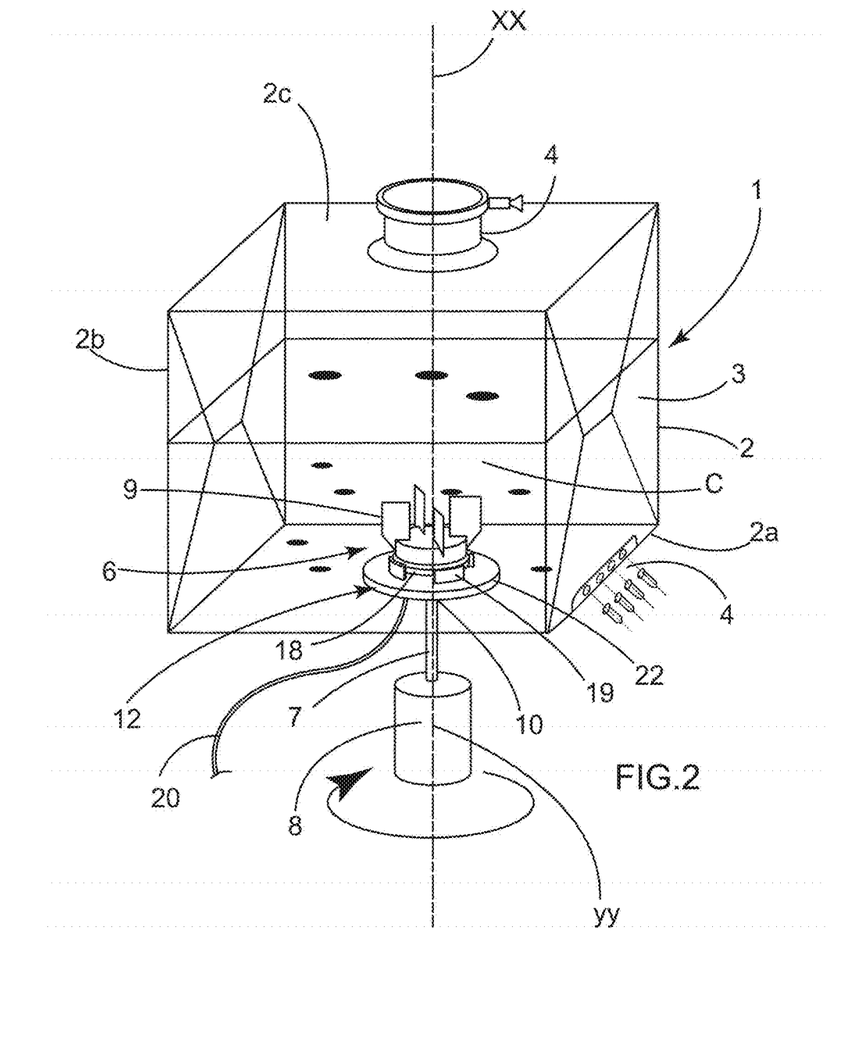
FIG. 2 is a schematic perspective view of a possible embodiment of a biopharmaceutical container such as a pouch for storing and/or filling and/or manipulating and/or transporting and/or mixing a biopharmaceutical content, the rigid external holding device of which is not shown.

FIG. 2 shows a biopharmaceutical container 1 being here a storage and/or filling and/or manipulation and/or transportation and/or mixing pouch intended to receive a biopharmaceutical content C, comprising at least one liquid phase and, where applicable, one or more components that may be in the solid phase, such as powder, for future mixing. For this purpose, an aim is to measure a parameter representative of the mixture such as for example conductivity.

In addition and where applicable, it is aimed to measure the temperature of the content C.

The container 1 has a principal axis XX which, in the normal position of use of the container 1, is situated in the middle and placed vertically.

The container 1, having a certain flexibility, is formed and delimited by a wall 2 having a certain flexibility, in one or more sections secured to one another for example by wells, having a bottom part 2a, a lateral part 2b and a top part 2c, delimiting an internal space 3 able to receive a certain quantity of the content C.

According to one embodiment, the container 1 is for single use and the wall 2 is a film made from plastics material.

The container 1 may have a greater or larger capacity, ranging up to 5,000 liters, according to the requirements and applications.

Because of the flexible nature of the container 1, it is placed in and held by a rigid or optionally semi-rigid external receptacle, not shown, when filled with its content C, the container matching the internal faces of the receptacle, while the geometry, shape and dimensions of the container 1 are suited to those of the rigid external receptacle.

Unless the context requires otherwise, the words "vertical", "horizontal", "top", "bottom", refer to the situation in which the container 1 is in a position suitable for operating. It is understood however that the container 1 may occupy other positions or have other states, for example because it is not in operation. The word "vertical" is not limited to its narrow literal sense but usually means what goes from the highest to lowest or vice-versa.

The word "axial" usually refers to what extends in the general direction of the axis concerned (axis XX or axis YY).

The word "transverse" usually refers to what extends in a general direction orthogonal to the axis concerned (axis XX or axis YY).

In general terms, the words "internal" and "external" refer respectively to what is located inside and outside the volume of the means concerned. Unless the context requires otherwise, they refer to the container 1.

The container 1 comprises one or a plurality of introduction and drainage through ports 4 respectively able to be closed or opened according to requirements. Pipes, pouches and reservoirs 5 may be associated, in fluid sealed communication, where necessary removable, with the ports 4.

In the embodiment more especially described here, a means 6 for mixing the content C located at least partly in the internal space 3 is associated with the container 1. Such a mixing means 6 comprises a trunnion or shaft 7, axial, able to be driven in rotation by a motor means 8, and carrying one or more mixing members 9, such as blades. It is this member 9 or these members 9, as well as the shaft 7, that are placed in the internal space 3.

One or more support or guide means 10 are provided, able to support or guide the trunnion 7. Such a support or guide means 10 is itself carried directly or indirectly, in whole or in part, by the wall 2 of the container 1.

In the embodiment shown in FIG. 1, the motor means 8 is placed in an upper position above the container 1, the trunnion 7 extends from the top part 2c of the container 1, where a support or guide means 10 is located, in the direction of the bottom part 2a, and the mixing members 9 are located at the middle part of the container 1, separated from the bottom part 2b.

In the embodiment shown in FIG. 2, the motor means 8 is placed in a lower position below the container 1, the trunnion 7 extends from the bottom part 2a of the container 1, where a support or guide means 10 is located, in the direction of the upper part 2c, and the mixing members 9 are located in the vicinity of the bottom part 2b of the container 1.

The trunnion 7, the motor means 8, the mixing members 9 and the support or guide means 10 may be the subject of various embodiments within the capability of a person skilled in the art. The same applies to their arrangement and association with the container 1.

Where necessary and as illustrated by FIG. 1, the container 1 may also comprise an aeration means 11 able to deliver to the content C a certain quantity of aeration gas located at least partly in the internal space 3 and in particular at least for its downstream end part in the bottom part 2a. Such an aeration means 11 may be the subject of various embodiments within the capability of a person skilled in the art. The same applies to its arrangement and association with the container 1.

The container 1 also comprises one (FIGS. 1 to 6, 8 to 10, 12 and 13) or several (FIGS. 7 and 11) devices 12 for sensing a parameter relating to an electrical phenomenon and able to be translated into an electrical signal for the biopharmaceutical content C, having an axis YY.

A parameter relating to an electrical phenomenon is a parameter that is per se of an electrical nature, such as conductivity, impedance or capacitance, or is obtained by a process that depends on a variable of an electrical nature, such as temperature (by means of a thermocouple or a resistance probe).

Such a sensing device 12 comprises support and fixing means 13, means 14 of capturing a parameter comprising a capture face 14a able to be in electrical contact with the content C when the sensing device 12 is carried by and associated with the container 1, and electrical connection means 15.

Hereinafter, the description of the sensing device 12 is made with reference to the case where the latter is associated with and in position on a container 1. However, it goes without saying that the invention relates both to the sensing device 12 alone, independently of its mounting on a container 1, and the assembly formed by the container 1 and the sensing device 12.

To enable the or each sensing device 12 to be mounted on and in the container 1, the wall 2 comprises one or more passage and mounting openings 16, having a periphery 16a, with which the sensing device or devices 12 cooperates or cooperate. The opening 16 is naturally adapted in size to the sensing device 12 with which it is intended to be associated. It is also adapted in its position on the container 1, namely located at the bottom part 2a of the container 1, where the sensing device 12 is also located. In doing this, the sensing device 12 may be located at a not great distance from, or even close to, the mixing means 6 and/or the aeration means 11, without its functioning being disturbed thereby.

The sensing device 12 has an axis YY which, in the embodiments shown in the figures, is coaxial with the axis XX, the axis YY also being the axial direction of the passage opening 16. However, the invention also relates to the cases where the axes XX and YY are not coaxial, being either parallel to each other or separated from each other by a greater or lesser distance or inclined with respect to each other by a greater or lesser angle.

Unless the context requires otherwise, the word "proximal" relating to the sensing device 12 or a member constituting it refers to what is or is able to be directed towards the biopharmaceutical container 1, (in particular the inside of the container 1) when the sensing device 12 mounted thereon. Conversely, the word "distal" refers to what is or is able to be directed in the opposite direction to the biopharmaceutical container 1 (in particular the outside of the container 1).

In the embodiment more especially described here, the content C is subject to a certain agitation, or even to a fairly powerful agitation, because of the operation of the mixing means 6 or the aeration means 11 and the presence of a member thereof in the internal space 3 in the vicinity where applicable of the sensing device 12. Such an agitation could compromise the exactitude and reproducibility of the capture of the parameter by the capture face 14a in electrical contact with the content C. To overcome this problem, provision is made for the sensing device 12 to comprise also a holding chamber 17, defining an internal space 17a, able to provide a certain confinement of the content C, the capture face 14a being positioned in the holding chamber 17, namely in its internal space 17a.

The reference 3a designates the part of the internal space 3 of the container 1 that is external to the holding chamber 17.

Thus the holding chamber is isolated from the internal space 3a and preserved from the agitation prevailing therein, by an internal chamber end wall 30 that is solid, that is to say closed, which will be detailed later, so as to minimise the impact of this agitation on the measurement of the parameter of the content C by the capture face 14a.

On the one hand the internal space 17a of the holding chamber 17 is in fluid communication with the internal space 3a of the container 1 via one or more open parts 18 of the holding chamber 17, able to provide passage of the content C between the internal space 17a of the holding chamber 17 and the internal space 3a of the container 1, and vice-versa, as well as a certain homogenisation of the content C between the two spaces 3a and 17a.

On the other hand, the internal space 17a of the holding chamber 17 is arranged in order to be isolated from the internal space 3a of the container 1 and the holding chamber 17 is arranged accordingly, taking into account the container 1, more especially comprising the internal chamber end wall 30, which is solid, that is to say closed.

"Isolated" means that there is, between the internal space 3a of the container 1 and the internal space 17a of the holding chamber 17, a physical separation—the internal chamber end wall 30, which is solid, that is to say closed—, suitable for—and whose function is—that the agitation prevailing in the internal space 3a is very appreciably attenuated, or even almost eliminated, in the internal space 17a. This physical separation is achieved by means of the internal chamber end wall 30, which is solid, that is to say closed, and closed parts 19 of the holding chamber 17, which include the open parts 18 located somewhere other than on the internal chamber end wall 30. Thus the impact of the agitation prevailing in the internal space 3a of the container 1 on the measurement of the parameter of the content C by the capture face 14a in the internal space 17a of the holding chamber 17 is minimised, even if the sensing device 12 is close to the mixing means 6 or aeration means 11.

The sensing device 12 is fixed rigidly and sealingly to the container 1, or more precisely to its wall 2, around the passage opening 16, or more precisely on its periphery 16a, for example by a fixing means 28 such as a bonding means or a welding means, interposed on a continuous contour between them. Thus it has, once mounted on the container 1, a proximal side able to be directed towards the container 1 and a distal side able to be directed in the opposite direction to the container 1.

Moreover, the sensing device 12 is in electrical communication firstly with the content C by and by means of the capture face 14a and secondly via the electrical connection means 15, through electrical connection means 20 located outside the container 1. Electrical communication means 21, such as contacts, printed circuits or the like, provide the electrical communication between the capture face 14a and the electrical connection means 15, which are located in the immediate vicinity of each other or distant to a greater or lesser extent.

The support and fixing means 13 are of a wall type. They are rigid and able to support the members constituting the sensing device 12 and to be fixed rigidly and sealingly to the wall 2 of the container 1 at the periphery 16a of its passage opening 16 by the fixing means 28.

The means 14 of capturing the parameter and the electrical connection means 15 are rigidly fixed to the support and fixing means 13, in particular more or less incorporated in them. For example, the support and fixing means 13 are integrated or incorporated in one way or another on the means 14 of capturing the parameter and the electrical connection means 15, or these means 14 and 15 are inserted in the support and fixing means 13.

Whereas the parameter capture means 14 are located in the internal space 3, and more precisely in the internal space 17a, the electrical connection means 15 are located outside the container 1 and are able to be accessible from the outside of the container 1 when the sensing device 12 is fixed to it.

The holding chamber 17 is delimited by the support and fixing means 13 configured with one or more closed parts 19 including one or more open parts 18, as previously indicated.

The support and fixing means 13 comprise at least one wall 22 referred as the support and fixing wall and, forming a rigid whole with it, in its middle area, a set 23 of chamber walls. Typically, the support and fixing wall 22 and the set 23 of chamber walls form a plastic moulded or injected part, in a single piece, having, with regard to the support and fixing wall 22 and the set 23 of chamber walls, a certain rigid strength.

The support and fixing wall 22 is closed, that is to say without any opening.

The support and fixing wall 22 has a roughly flat shape, at least in part.

It is placed transversely, at least in part, with respect to the axial direction YY of the sensing device 12 and the passage opening 16 of the container 1.

The support and fixing wall 22 is delimited by a peripheral external edge 24 and comprises two faces 25a and 25b, one of which, 25a, comprises a peripheral area 25c for rigid and fluidtight fixing to the wall 2 of the container 1 at the periphery 16a of the passage opening 16, and where the fixing means 28 is located.

Turning now to the walls of the set 23 of chamber walls, these are adjacent to one another and delimit the holding chamber 17. In addition, the walls of the set 23 of chamber walls comprise the closed parts 19 including the previously mentioned open parts 18.

The support and fixing means 13 comprising the support and fixing wall 22 and the set 23 of chamber walls may be the subject of various embodiments.

In the embodiments shown on the figures, the set 23 of chamber walls comprises, forming a rigid whole, at least one wall 26 referred to as the external chamber axial end wall (or external chamber end wall) and a wall 27 referred to as the peripheral chamber wall. It also comprises the internal chamber end wall 30, which is solid, that is to say closed, already mentioned.

The external chamber end wall 26 is solid, that is to say closed, without any opening. It is placed transversely, at least in part, with respect to the axial direction YY of the sensing device 12 and the passage opening 16 of the container 1. It is able to come into line with the passage opening 16 of the container 1 and its function is at least to help to close it. The wall 26 is termed external since one of its faces is located outside the container 1, while the other face, opposite, is located in the internal space 17a of the holding chamber 17, the wall 26 thus also constituting the wall delimiting the container 1. The wall 26 is termed the external chamber axial end wall since it forms the closed end part of the holding chamber 17 that is distal and located towards the outside of the container 1.

Figure 12:
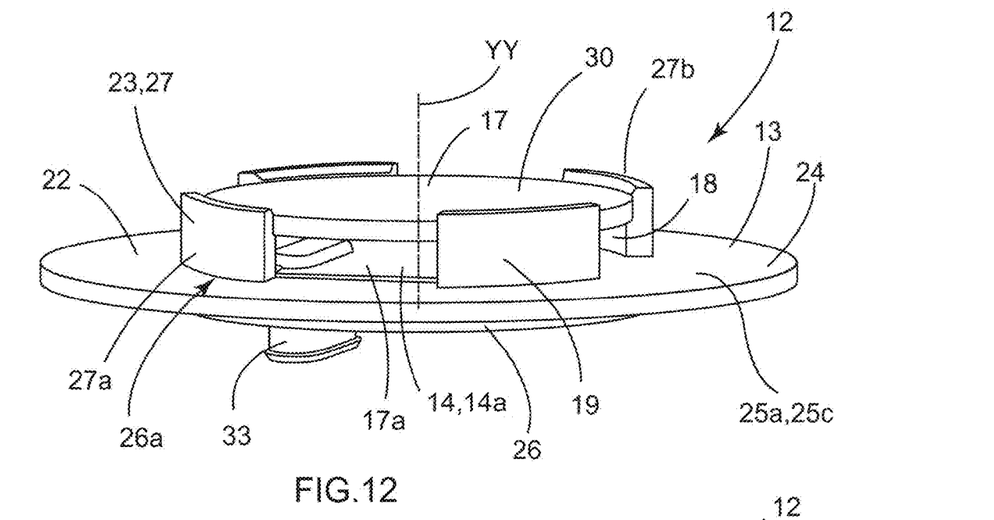
FIGS. 12 and 13 are two perspective side views of a possible embodiment of the sensing device, respectively seen from the proximal side and the distal side, said embodiment being structurally close to that of FIG. 3, except that the sensing device includes a means of supporting or guiding a trunnion of a mixing means in the case of FIG. 3 but not in that of FIGS. 12 and 13, while the sensing device includes a cavity for protecting the electrical connection means in the case of FIGS. 12 and 13, but not in that of FIG. 3.

The peripheral chamber wall 27 extends from the periphery 26a (FIG. 12) of the external chamber end wall 26. From its distal axial end part 27a (FIG. 12), adjacent to the external chamber end wall 26, the peripheral chamber wall 27 extends at least partly roughly in the axial direction YY towards the proximal side of the container 1, that is to say towards the inside of the latter, and comprises a proximal axial end part 27b (FIG. 12).

Figure 3:
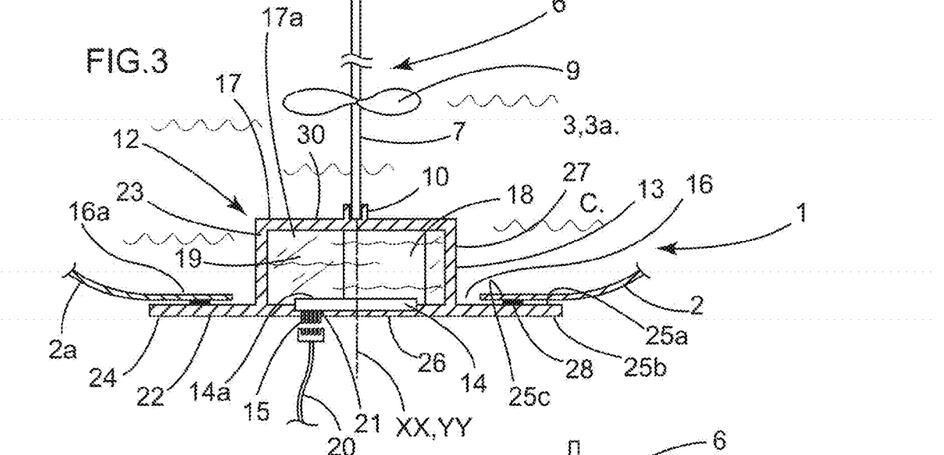
Figure 4:
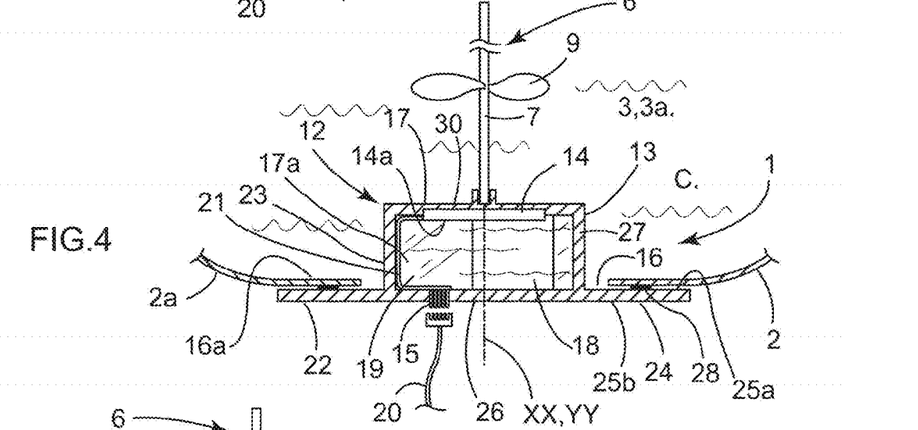
Figure 5:
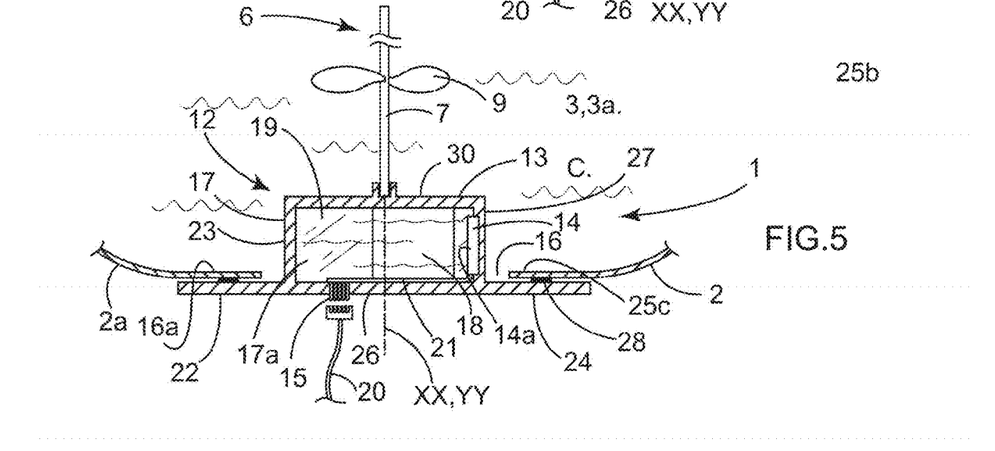
Figure 13:
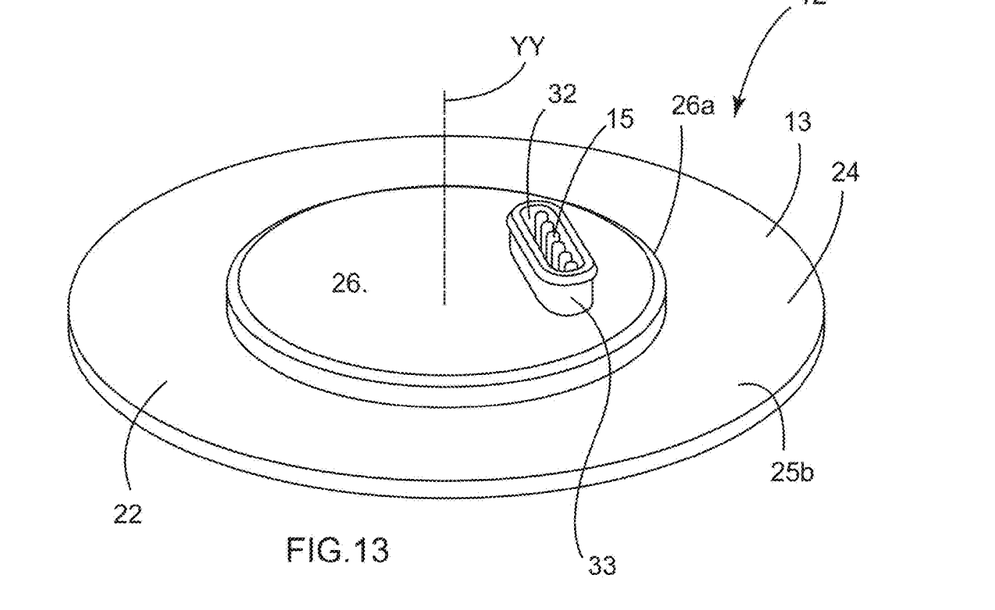

Reference is now made more especially to FIGS. 3 and 13, which show two functionally similar embodiments. In these embodiments, the support and fixing wall 22 and the external chamber end wall 26 are the two structurally distinct substantially coplanar parts of the same wall. The wall 22 being its annular periphery and the wall 26 being its central part. The same arrangement is found in the embodiments shown in FIGS. 4, 5 and 7.

In other embodiments (FIGS. 6, 8 to 11), the external chamber end wall 26 and the support and fixing wall 22 are offset in a roughly axial direction (along the axis YY) and are connected to each other by a wall 29 referred to as the peripheral connecting wall, which extends, at least partly, in the roughly axial direction.

Figure 6:
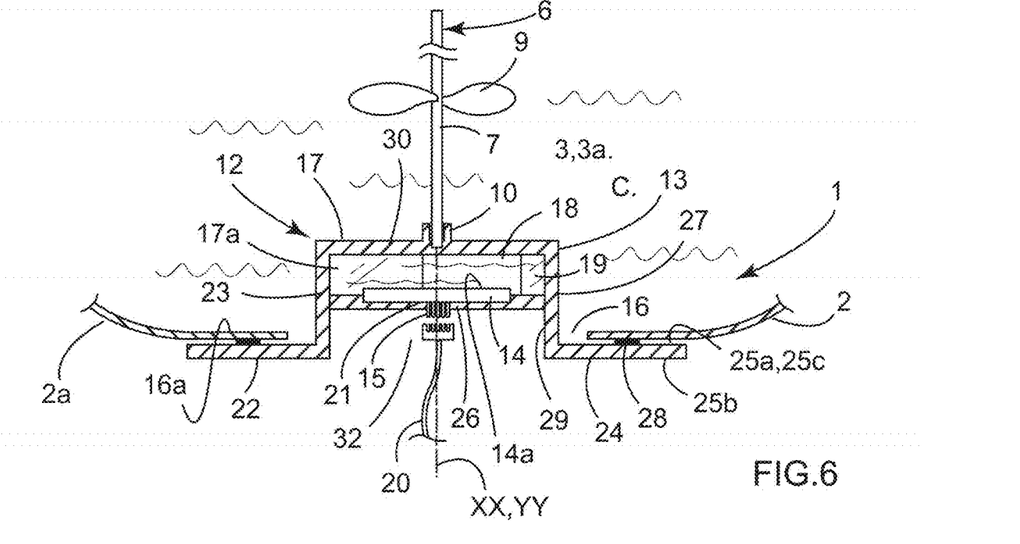

For example, in the embodiment in FIG. 6, the external chamber end wall 26 is proximal, while the peripheral connecting wall 29 extends towards the proximal side with respect to the support and fixing wall 22.

In the embodiments in FIGS. 8 to 11 on the other hand, the external chamber end wall 26 is distal while the peripheral connecting wall 29 extends towards the distal side with respect to the support and fixing wall 22.

Reference is now made more especially to FIGS. 3 to 7 and 9 to 11 in which the set 13 of chamber walls also comprises the internal axial end wall 30 of the chamber (or internal chamber end wall), forming a rigid whole, which is here placed transversally with respect to the axial direction YY of the sensing device 12 and the passage opening 16 of the container 1. The internal axial chamber end wall 30 is located at least partly in line with the external chamber end wall 26. The internal axial chamber end wall 30 is adjacent to the proximal end part 27a of the peripheral chamber wall 27. In these various embodiments, the open parts 18 are formed in the peripheral chamber wall 27, but not in the internal chamber end wall 30, which is solid, that is to say closed.

Figure 8:
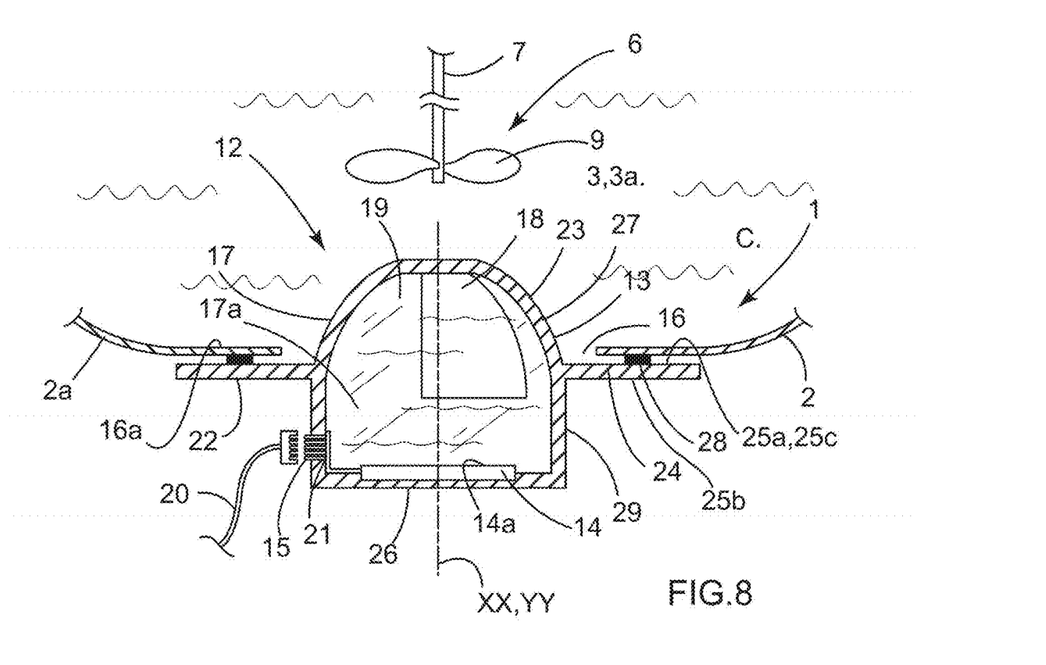
Figure 9:
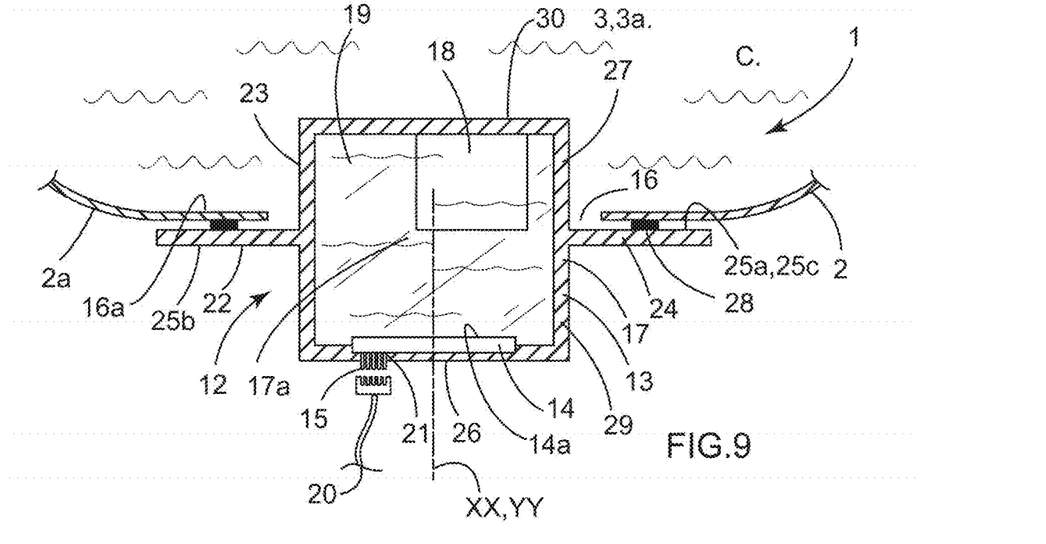
Figure 10:
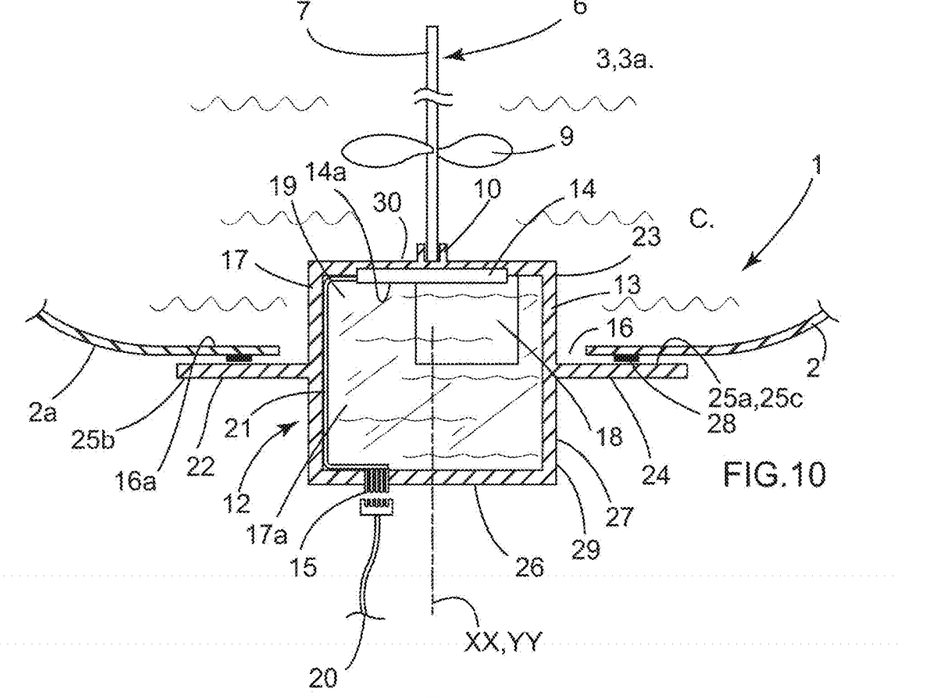

Reference is now made more especially to FIG. 8, in which the set 13 of chamber walls also comprises a wall 30 having a curved extension for connection with the peripheral chamber wall 27, the open parts 18 being provided laterally, but not in the internal chamber end wall 30, which is solid, that is to say closed.

The holding chamber 17 consequently extends between the external chamber end wall 26 on one axial side, the internal chamber end wall 30 on the other axial side, both solid, that is to say closed, and extends laterally to the peripheral chamber wall 27 which either fulfils only this function (FIGS. 3 to 7) or in whole or in part fulfils the function of the peripheral connecting wall 29 (FIGS. 8 to 11). In both cases, the peripheral chamber wall 27 comprises the open parts 28.

As indicated, the parameter-capture face 14a is positioned in the holding chamber 17, namely in its internal space 17a, and thus it is in electrical contact with the content C situated in the internal space 17a of the holding chamber 17. More precisely, the capture face 14a is entirely located in the holding chamber 17, on at least one face of the external chamber end wall 26 (FIGS. 3 and 6 to 9) or of a wall of the set 23 of chamber walls (FIGS. 4, 5 and 10) or on both (FIG. 11), said capture face 14a being turned towards the inside of the holding chamber 17 in order to be located in its internal space 17a. With regard to the set 23 of chamber walls, the capture face 14a is located on the face turned towards the inside of the peripheral chamber wall 27 (FIG. 5) or the internal chamber end wall 30 (FIGS. 4 and 10) or on both.

According to one embodiment (FIGS. 3 to 11), the capture face 14a is located in line with a closed part of the set 23 of chamber walls and/or the external chamber end wall 26.

According to a feature shown in the figures in relation with one embodiment of the invention, the capture face 14a is substantially flat and coplanar with the substantially flat internal face of the wall on which it is located 26, 27, 30.

According to one embodiment, the capture face 14a is close to a closed part 19 of a wall facing the set 23 of chamber walls or close to the external chamber end wall 26 and/or is separated from an open part 18. This structural arrangement has the effect that the agitation in the internal space 17a of the holding chamber 17 is very much attenuated, or almost non-existent, compared with that existing in the internal space 3a.

Figure 7:
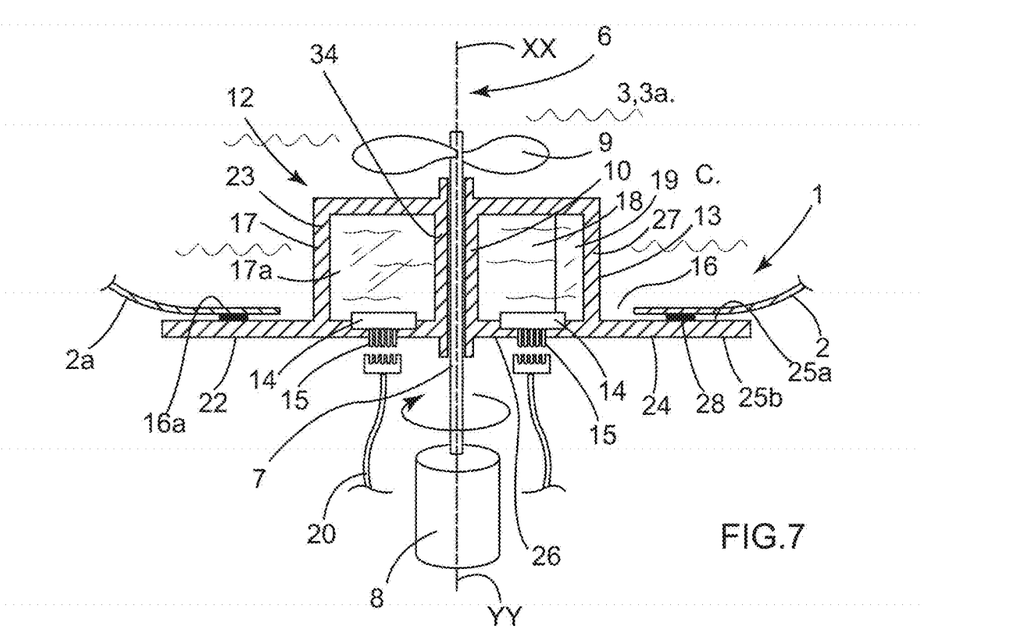
Figure 11:
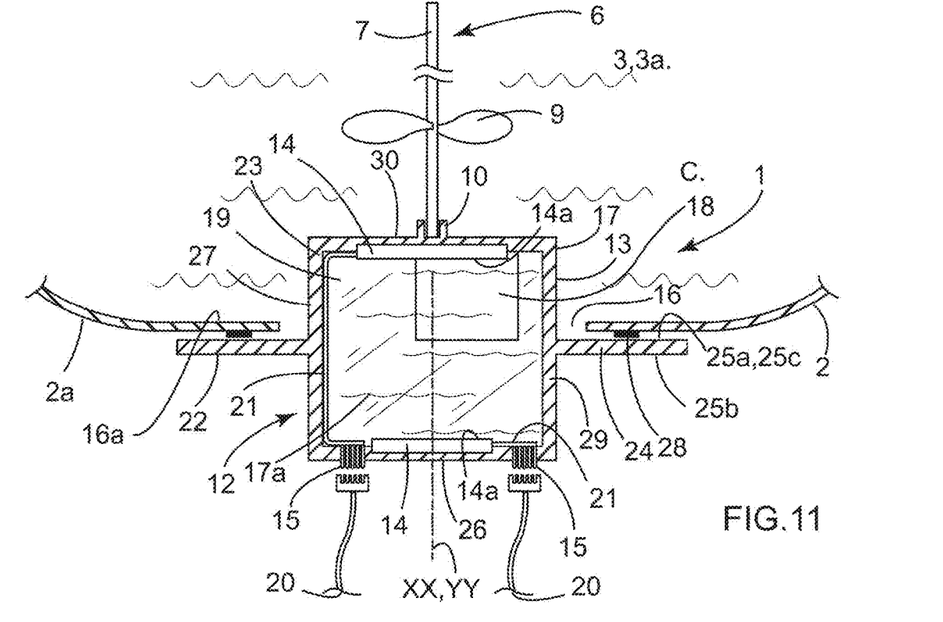

Reference is made to FIGS. 3 to 6 and 8 to 10, which illustrate a sensing device 12 that comprises a single capture means 14 for a parameter. In the case of FIGS. 7 and 11, the sensing device 12 on the other hand comprises a plurality of capture means 14. This plurality of capture means 14 is intended to capture a single parameter (for example for security purposes) or several parameters. Such an arrangement is particularly useful when the value of a first parameter is linked to that of a second. For example, it is possible, by virtue of this arrangement, to capture the conductivity and the temperature at which the conductivity was captured.

In such an embodiment and according to various arrangements, the capture faces 14a in the plurality of capture faces of the plurality of capture means 14 are located on the face turned towards the inside of the chamber of the same wall—in this case in the case of FIG. 7, the external chamber end wall 26—or of different walls—in this case in the example of FIG. 11, the external chamber end wall 26 and the internal chamber end wall 30—. More generally, the plurality of capture faces 14a are located on the walls 26, 27, 29 and 30, according to the configurations selected.

In the embodiments in FIGS. 3 to 7 and 9 to 11, the electrical connection means 15 are carried by the external chamber end wall 26. In the embodiment of FIG. 8, the electrical connection means are carried by the peripheral connecting wall 29. Naturally, when several electrical connection means 15 are provided, i these embodiments can be combined with one another.

In the embodiments of FIGS. 6 and 13, the electrical connection means 15 are housed in a protective cavity 32. Such a protective cavity is delimited by the external chamber end wall 26 and either the peripheral connecting wall 29 (FIG. 6) or a dedicated cavity wall 33 (FIG. 13). This structural arrangement protects the electrical connection means 15 from any damage that might result from a force being applied to them.

According to other embodiments (FIGS. 3 to 5 and 7 to 11), such a protective cavity for the electrical connection means 15 is not provided.

In the embodiments of FIGS. 3 to 6, 8 to 10 and 13, the sensing device 12 comprises a single set of electrical connection means 15. In the embodiments in FIGS. 7 and 11, the sensing device 12 comprises a plurality of electrical connection means 15. The latter embodiment usually goes together with the same plurality of capture means 14.

In the embodiment more especially described here, a mixing means 6 is usually associated with the container 1, the mixing means 6 comprising a trunnion or shaft 7 and one or more support or guide means 10 able to support or guide the trunnion 7.

According to one development of the invention illustrated by FIGS. 3 to 7 and 10 and 11, the sensing device 12 and said support or guide means 10 are integrated, the support and fixing means 13 including at least one such support or guide means 10. More particularly, such a support or guide means 10 is located on or carried by the support and fixing wall 10 and/or the set 23 of chamber walls. According to circumstances, and as illustrated in the drawings, a single support or guide means 10 is integrated in the sensing device 12. In other cases (not shown), several support or guide means 10 for several journals or shafts 7, in particular arranged parallel to each other, are integrated in a sensing device 12.

Reference is now made more especially to FIGS. 3 to 6 and 10 to 11, which illustrate an embodiment in which the support and guide means 10 forms, with the internal chamber end wall 30, a blind end bearing for the trunnion or shaft 7. The support or guide means 10, like the trunnion or shaft 7, is then placed above the holding chamber 17, and entirely outside it. This embodiment takes advantage of the fact that the internal chamber end wall 30 is solid, that is to say closed.

Reference is now made more especially to FIG. 7 which illustrates an embodiment in which the support or guide means 10 forms, with the support and fixing wall 22 and/or with the set 3 of chamber walls, a through bearing for the trunnion or shaft 7. The support or guide means 10, like the trunnion or shaft 7, is then located partly outside and partly inside the holding chamber 17. To prevent the trunnion or shaft 7 passing through the holding chamber 17 from creating an agitation, since it is precisely sought to minimise the agitation, it is possible to provide for example an annular wall 34, located at least partly inside the holding chamber 17, said wall 34 forming a protection for the trunnion or shaft 7.

By virtue of the arrangement of the support or guide means 10 and the sensing device 12, it is possible, without prejudice to the capture of the parameter or parameters, to place the sensing device 12 in a location where it is not far from the mixing means 6 and, where applicable, from the aeration means 11, or even where it is very close to it.

In order to produce biopharmaceutical containers 1 provided with sensing devices 12, a bare biopharmaceutical container 1 and sensing devices 12 are provided. By virtue of the invention, these sensing devices 12 can be calibrated in advance. Then, a sensing device 12 is mounted on a container 1, positioning it in the opening 16, and, finally, the support and fixing wall 22 is secured fixedly and sealingly to the wall 2 in the periphery 16a.

By selecting the structure, shape, arrangement and size of the holding chamber 17, it is possible to greatly minimise the effect resulting from the agitation caused by the mixing means 6 or the aeration means 11 when such exists.

The invention claimed is:

1. A device for sensing a mixture related parameter related to an electrical phenomenon and able to be translated into an electrical signal, in a biopharmaceutical content located in a space of a biopharmaceutical container delimited by a wall having an opening with a periphery, the biopharmaceutical content being able to be subject to agitation, the sensing device having an axis, a proximal side towards the container and a distal side opposite to the container, comprising: support and fixing means of a wall, rigid, able to support constituent members of the sensing device and to be fixed rigidly and sealingly to the wall at a periphery of an opening, comprising a support and fixing wall and a set of chamber walls, delimiting a chamber for the biopharmaceutical content, having a closed part that includes an open part to provide passage of the biopharmaceutical content between the chamber and an internal space of the container external to the chamber, said set of chamber walls comprising an external chamber end wall, closed, disposed transversely, with a periphery to come in line with the opening and at least one peripheral chamber wall, with a proximal axial end part, and extending from a distal end part in an axial direction towards a proximal side from said periphery of the external chamber end wall, and sensing means for capturing the parameter, rigidly fixed to the support and fixing means, comprising a capture face located in the chamber, to be in electrical contact with the biopharmaceutical content, and electrical connection means electrically connected to the sensing means, rigidly fixed to the support and fixing means, to be accessible from the outside of the container when the sensing device is fixed to it and to be electrically connected to electrical connection means located outside the container, the set of walls comprising an internal chamber end wall forming a rigid whole, solid, that is closed, disposed at least in part generally transversely in line with the external end wall from the proximal axial end part of the peripheral chamber wall, the open part being provided in the peripheral chamber wall, the chamber being a holding chamber to provide confinement of the content located therein, the chamber being isolated from the internal space and preserved from agitation prevailing therein by the internal chamber end wall, solid, closed, so as to minimize an impact of said agitation on measurements of the parameter of the content by the capture face.

2. The sensing device according to claim 1, in which the support and fixing wall is at least partly roughly flat in shape, delimited by a peripheral external edge which comprises two faces, and one of the faces of which comprises a peripheral area for rigid sealed fixing to the wall of the container at the periphery of its opening.

3. The sensing device according to claim 1, in which the support and fixing wall and the external end wall are two functionally distinct parts of a same wall.

4. The sensing device according to claim 1, in which the external end wall and the support and fixing wall are offset in a axial direction and connected to each other by a peripheral connecting wall, extending at least partly in the axial direction, extending with respect to the support and fixing wall towards the distal side or towards the proximal side.

5. The sensing device according to claim 1, in which the capture face is entirely located in the holding chamber on at least one face of the external end wall and/or of a wall in the set of walls, and is turned towards inside the holding chamber.

6. The sensing device according to claim 5, in which the capture face is located on the peripheral chamber wall and/or on the internal chamber end wall.

7. The sensing device according to claim 5, in which the capture face is located in line with a closed part of the set of walls and/or of the external end wall.

8. The sensing device according to claim 5, in which the capture face is substantially flat and coplanar with a substantially flat internal face of the wall on which the capture face is located.

9. The sensing device according to claim 5, in which the capture face is adjacent a closed part of a wall facing the set of walls or the external end wall of the chamber and/or at a distance from an open part.

10. The sensing device according to claim 1, which comprises a plurality of means of capturing one or more parameters.

11. The sensing device according to claim 10, in which the captures faces in the plurality of capture faces of the plurality of capture means are located on the face turned towards the inside of the holding chamber of the same wall or different walls.

12. The sensing device according to claim 1, in which the electrical connection means are carried by the support and fixing wall and/or the external end wall and/or a peripheral connecting wall.

13. The sensing device according to claim 1, in which the electrical connection means is housed in a protective cavity.

14. The sensing device according to claim 13, in which the protective cavity is delimited by the external wall and either a peripheral connecting wall ort a dedicated cavity wall.

15. The sensing device according to claim 1, which comprises a plurality of electrical connection means.

16. The sensing device according to claim 1, in which the sensing means is means of sensing the conductivity, impedance, capacitance or temperature of the biopharmaceutical content.

17. The sensing device according to claim 1, in which the support and fixing wall has a certain rigid strength.

18. The sensing device according to claim 1, in which the support and fixing means include at least one support or guide means able to support or guide at least one trunnion of a mixing means.

19. The sensing device according to claim 18, in which the at least one support or guide means is located on or carried by the support and fixing wall and/or the set of chamber walls.

20. The sensing device according to claim 19, in which at least one support or guide means forms, with the support and fixing wall and/or the set of chamber walls, a blind end bearing for at least one trunnion of the mixing means.

21. The sensing device according to claim 1, the sensing device being for single use.

22. A biopharmaceutical container of the type comprising one or more inlets and outlets, at least one mixing means, an internal space delimited by a wall having at least one passage and mounting opening for at least one sensing device, biopharmaceutical content of the container being able to be subject to agitation, the at least one sensing device being fixed rigidly and sealingly to the container around the at least one passage opening and able to be in electrical communication firstly with the content and secondly with electrical connection means located outside the container, in which the at least one sensing device is a sensing device according to claim 1.

23. The biopharmaceutical container according to claim 22, in which the at least one mixing means comprise at least one member located in the internal space.

24. The biopharmaceutical container according to claim 22, in which a sensing device is near the at least one mixing means.

25. The biopharmaceutical container according to claim 22, in which a sensing device is located at a bottom part of the biopharmaceutical container.

26. The biopharmaceutical container according to claim 22, in which the wall of the biopharmaceutical container has a certain flexibility.

27. The biopharmaceutical container according to claim 22, the biopharmaceutical container being for single use.

28. The biopharmaceutical container according to claim 22, which constitutes a pouch for storing and/or filling and/or manipulating and/or transporting and/or mixing the biopharmaceutical content or a bioreactor for the biopharmaceutical content.

29. The biopharmaceutical container according to claim 22, further comprising at least one aeration means.

30. The biopharmaceutical container according to claim 29, wherein the at least one aeration means comprise at least on member location in the internal space.

31. The biopharmaceutical container according to claim 29, wherein the sensing device is adjacent the at least one sensing means.

* * * * *